United States Patent [19]

L'Esperance

[11] Patent Number: 4,669,466
[45] Date of Patent: Jun. 2, 1987

[54] METHOD AND APPARATUS FOR ANALYSIS AND CORRECTION OF ABNORMAL REFRACTIVE ERRORS OF THE EYE

[75] Inventor: Francis A. L'Esperance, Englewood, N.J.

[73] Assignee: LRI L.P., New York, N.Y.

[21] Appl. No.: 691,923

[22] Filed: Jan. 16, 1985

[51] Int. Cl.$^4$ .............................................. A61B 17/00
[52] U.S. Cl. ................................ 128/303.1; 128/395; 364/413; 358/98
[58] Field of Search ..................... 128/645, 745, 303.1, 128/660; 358/96, 98; 364/413, 488–491; 340/709, 710

[56] References Cited

U.S. PATENT DOCUMENTS

| | | | |
|---|---|---|---|
| 3,214,515 | 10/1965 | Eberline | 358/96 |
| 3,558,814 | 1/1971 | Engle | 358/96 |
| 3,598,977 | 8/1971 | Clemmons | 364/488 |
| 3,643,219 | 2/1972 | Heimann | 340/709 |
| 3,677,074 | 7/1972 | Murr | 128/645 |
| 3,711,642 | 1/1973 | Jatteau | 358/96 |
| 3,735,036 | 5/1973 | Macovski | 358/96 |
| 3,739,347 | 6/1973 | Forsberg | 340/709 |
| 3,769,963 | 11/1973 | Goldman et al. | 128/303.1 |
| 3,982,541 | 9/1976 | L'Esperance | 128/303.1 |
| 4,101,961 | 7/1978 | Reiber | 358/96 |
| 4,173,980 | 11/1979 | Curtin | 128/303.1 |
| 4,200,869 | 4/1980 | Marayama et al. | 340/701 |
| 4,259,725 | 3/1981 | Andrews et al. | 340/709 |
| 4,336,809 | 6/1982 | Clark | 128/303.1 |
| 4,461,294 | 7/1984 | Baron | 128/303.1 |
| 4,481,664 | 11/1984 | Linger | 364/489 |
| 4,580,121 | 4/1985 | Myers | 128/660 |

FOREIGN PATENT DOCUMENTS

| | | | |
|---|---|---|---|
| 37663 | 10/1981 | European Pat. Off. | 364/489 |
| 0083494 | 7/1983 | European Pat. Off. | |
| 0111060 | 6/1984 | European Pat. Off. | |
| 1288245 | 1/1969 | Fed. Rep. of Germany | |
| 2937598 | 3/1981 | Fed. Rep. of Germany | 128/395 |
| 3148748 | 7/1983 | Fed. Rep. of Germany | 128/303.1 |
| 782810 | 11/1980 | U.S.S.R. | |

OTHER PUBLICATIONS

"Ultrasonics in Clinical Diagnosis", ed. by Wells Chap. 5, Ultrasonic Investigations in Opthalmology, by Giglio pub. 1977, pp. 87–96.
Scan Literature 1981.
Story Literature 1/82.
"Excimer Laser Surgery of the Cornea", by Trokel et al. Am. J., Opthal. 96:710-715, 1983.
Operating Instructions for the Kreaner Coneometer 2/81.
"Advanced Techniques in Opthalmic Microsurgery", by Girard, pub. 1981, pp. 84,107–110, 114, 116, 123, 125–133, 143–171.
"Computer Assisted Mapping with the Light Microscope", by Forbes et al., J. of Neuroscience Methods, vol. 1, No. 1, 3/79, pp. 77–94.
"Computer Graphics in Power Plant Design", by Strong et al. Power Engineering Society Summer Meeting 1978
"The Use of Interactive Computer Graphics in the analysis of Structures", by Argyris et al.; Angewandte Informatic 4/72.
Laser Focus, vol. 18, No. 1, Jan. 1982, pp. 57–58, H. T. Powell: "Excimers".
Laser Focus, vol. 20, No. 10, Oct. 1984, pp. 104, 106, Goldman: "Laser Surgery and Medicine in the next Decade".
Revue de Physique Appliquee, vol. 15, No. 9, Sept. 1980, pp. 1417 to 1426, Paris, France, Brunetaud, et al., "Les Applications Therapeuticques des Lasers".

*Primary Examiner*—Kyle L. Howell
*Assistant Examiner*—David Shay
*Attorney, Agent, or Firm*—Hopgood, Calimafde, Kalil, Blaustein & Judlowe

[57] ABSTRACT

The invention contemplates instrumentation to aid in performing refraction-corrective surgery on the conrea, (1) by determining the topography of the anterior surface of the cornea, the determination being in the form of digitized data entered into computer storage, (2) by determining the local thickness of the cornea along multiple axes, the determination being also in the form of digitized data entered into computer storage, and (3) by providing a CAD/CAM display of both categories of data, correlated as appropriate for the surgeon's selective display of a corneal region, aspect or section, as the surgeon may deem pertinent to a prospective operation.

13 Claims, 6 Drawing Figures

45° MERIDIAN

METHOD AND APPARATUS FOR ANALYSIS AND CORRECTION OF ABNORMAL REFRACTIVE ERRORS OF THE EYE

BACKGROUND OF THE INVENTION

The invention relates to non-invasive ophthalmogical instrumentation and techniques for determining physical dimensions of an eye and to the informed use of thus-derived dimensional data in the performance of corrective surgery upon the cornea.

The human eye is an extremely powerful focusing device that produces an image on the surface of the retina. The focusing elements of the eye are the cornea and the lens. The cornea accounts for approximately 80 percent of the focusing ability (48 diopters) and the lens approximately 20 percent (12 diopters). In the case of myopia, the eye is assumed to have a longer egg-like shape in which case the light beam focuses to a spot located in front of the retina and therefore is out of focus. In hyperopia, the focusing system is inadequate, and the focusing spot and image are located behind the retina and also out of focus. In the case of astigmatism, a spot or clear image is not created, and the eye basically focuses at two areas behind or in front of the retinal surface. In order to correct myopia, hyperopia, or astigmatism, spectacles or contact lenses are used to place the image directly on the rods and cones of the retina. As an alternative to artificial correction (i.e., spectacles, or contact lenses), it has been demonstrated, as noted previously, that refractive keratoplasty, surgically altering the shape of the cornea, will achieve the same result.

As alternative techniques of refractive keratoplasty, radial keratotomy and corneal sculpting are the two kinds of corneal surgery which have been receiving increased consideration. In radial keratotomy, some 8 to 32 radial incisions are applied with a knife to the cornea, and it has been shown that the curvature of the cornea is thereby flattened to a degree which places the focus further back in the eye, hopefully near the retinal surface. Such an operation has been demonstrated to improve vision by reducing objective myopia, with a measured improvement of up to 12 diopters. The operation is performed by using a diamond or ruby knife with an adjustable belt or sleeve which controls the depth of incision to fractions of a millimeter.

The extent of myopia correction is determined by the depth of cut, the number of radial incisions, and the proximity of the incisions to the center of the cornea. Various other incisions have been combined with radial incisions to achieve other corrective effects, and by combining circumferential incisions with radial incisions in various portions of the cornea, a characterized flattening of the cornea is possible, whereby a concurrent decrease is achieved in myopia as well as in astigmatism.

Corneal sculpting consists of an advanced procedure, beyond radial keratotomy, which involves the removal of external layers of the cornea, in such a way as to affect the radius of curvature in order to increase or decrease the dioptric power of the front surface of the cornea. By removing various layers of the cornea to the extent of 0.15 to 0.25 millimeters of the 0.60-millimeter thickness of a cornea, up to 12 diopters of myopia or hyperopia can be corrected, along with correction of extremely high degrees of astigmatism (or unevenness of the cornea). By thus sculpting the cornea, in effect, the outer surface of the cornea can have the radius of curvature of a correcting contact lens, as if the contact lens had been inserted over the malformed cornea. It is the outer surface of the cornea with its air/cornea interface that provides the increase or decrease in the focal length (power) of the cornea and therefore alters the refractive state of the eye.

One approach to corneal sculpting has been a procedure termed keratomileusis, whereby the exterior of the cornea is removed as a plano-convex button, frozen, placed on a microlathe, and shaped by the lathe under computer control until a predetermined curvature of the cornea is achieved. The corneal button is then thawed and sewn back onto the patient's eye. In this way, the external corneal curvature is changed by a process of mechanical intervention.

Another approach to corneal sculpting and to radial keratotomy is via laser ablotion, as described in my copending patent application Serial No. 552,983, filed Nov. 17, 1983. From the aspect of corneal sculpting, said patent application describes methods and apparatus for changing the anterior surface of the cornea from an initial curvature having defective optical properties to a subsequent curvature having correctively improved properties, by using ultraviolet laser radiation to selectively ablate the anterior surface of the cornea by photodecomposition, with penetration into the stroma and volumetric sculpturing removal of corneal tissue to such penetration depth and profile as to characterize the anterior surface of the cornea with said subsequent curvature. And for performing a radial keratotomy, said patent application discloses use of a scan-deflectable ultraviolet laser beam to execute a radial incision through the anterior surface of the cornea, with ablative penetration of the stroma, at each of a plurality of angularly spaced orientations on the anterior surface.

But no matter what the procedure for operating upon the cornea to achieve refractive correction, the fact remains that what has been done and is being proposed to be done is largely experimental. There is no fund of experience upon which to draw for an acceptably accurate prediction of ultimate refractive correction in the eye, for a given technique in application to a given category of corneal dimensions. And, particularly in the case of radial keratotomy, the danger is ever present that incision will be made to excessive depth, thus aborting the otherwise non-invasive nature of the operation.

BRIEF STATEMENT OF THE INVENTION

It is an object of the invention to provide an improved method and apparatus for use in aid of non-invasive corneal surgery to achieve refractive correction of an eye.

A specific object is to provide the ophthalmological surgeon with corneal thickness and topography data, for a particular abnormal eye, and in the form of readily interpretable context against which to determine the depth of surgical incision and the surface distribution of surgical incision into the anterior surface of the abnormal cornea, to achieve a desired refractive correction.

Another specific object is to achieve the above objects with a CAD/CAM visual display of corneal topography and thickness, with selective availability of the display for various attitudes.

Still another specific object is to achieve the above objects with a visual display which also indicates, for selected attitudes, the extent of corneal excision required to achieve a particular refraction-corrected result, e.g., emmetropia (perfect vision at distance).

It is also a specific object to meet above objects with computer-aided means for prescribing for a given examined eye the nature and extent of refraction-corrective corneal surgery required to achieve or to substantially achieve emmetropia for the examined eye.

A further specific object is to meet the above objects with computer-aided means whereby digital data are available for control of automated apparatus to perform the refraction-corrective surgery.

The foregoing objects and further features are achieved (1) by determining the topography of the corneal surface of an eye, the determination being in the form of digitized data entered into computer storage, (2) by determining the local thickness of the cornea along multiple axes, the determination being also in the form of digitized data entered into computer storage, and (3) by providing a CAD/CAM display of both categories of data, correlated as appropriate for the surgeon's selective display of a corneal region, aspect or section, as he may deem pertinent to a prospective operation.

DETAILED DESCRIPTION

The invention will be illustratively described in detail in conjunction with the accompanying drawings, in which.

Figure 1:
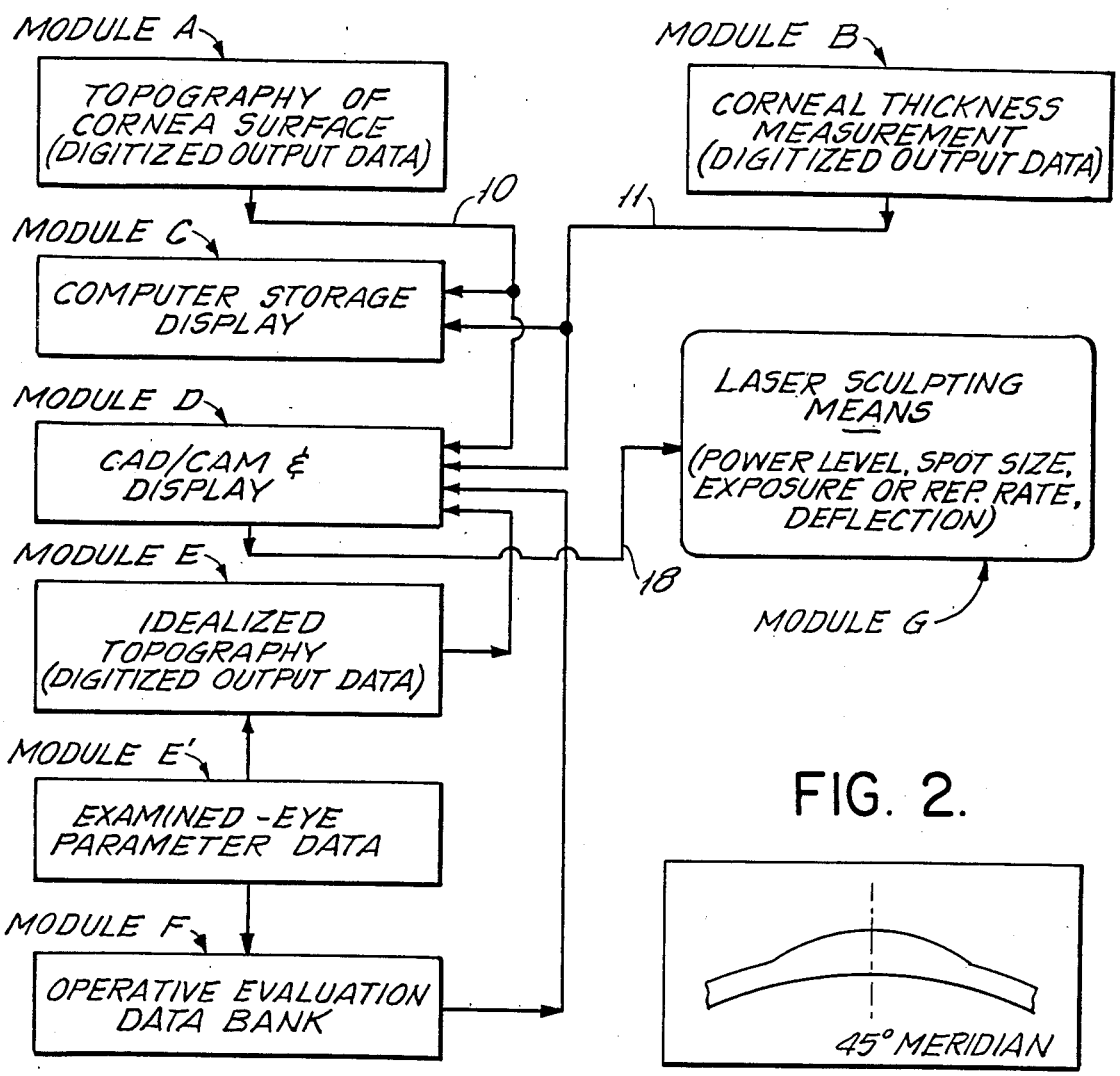
FIG. 1 is a block diagram schematically indicating apparatus and manipulative steps involved in the invention.

The diagram of FIG. 1 depicts all components for performing corneal evaluation and analysis, as well as those involved in incisional or sculpting keratoplasty operations which are based on the analysis.

The evaluation portion is shown to comprise three modules A, B, and C. The first, module A, determines topography of the cornea surface of the eye under consideration. This module may be an optical ocular scanner or a photokeratometer, with provision for generation of digitized topography data in an output 10. Module A has the ability to rapidly scan the cornea in such a way as to determine the entire topography of the outer surface of the cornea, from limbus to limbus. In this module, subtle differences in curvature of the outer cornea or inner optical zone are precisely and clearly defined, and the module will be understood to include an analyzer having the capability of digitizing the data from thousands of individual points on the particular cornea. A suitable equipment for use in Module A is the PKS-1000 photokeratoscope commercially available from the Japanese firm, Sun Contact Lens Co., Ltd., with U.S. offices in Palo Alto, Calif. The Sun photokeratoscope is available with a photo-analyzer having a digitized output from which visual display is produceable to show the cross-sectional profile of anterior-surface curvature, for any cross-sections which include the central axis of the eye; the connection 10 will be understood to convey such a digitized output.

The second module B comprises pachymetric means for making multiple determinations of the precise thickness of the cornea, to within thousandths of a millimeter, at plural locations on the surface of the cornea. The data are generated by ultrasonic-ranging, and are digitized as to measured thickness correlated with location-coordinate data for supply in an output 11. The pachymeter measurements may be performed manually, on an individual point-by-point basis, using a commercially available hand-held transducer probe flexibly connected to power supply and display means, for example the Myopach ultrasonic pachymeter available from Myocure, Inc., Los Angeles, Calif., or the CILCO, Inc. "Villasenor" ultrasonic pachymeter, available from their Huntington, W. Va. location. In using such a device, a fixation target enables the unexamined eye of the patient to maintain central-axis stability for his examined eye when the probe is placed on the corneal surface anywhere from the central optical axis to the periphery.

Figure 3:
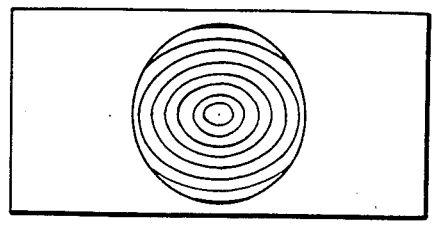

Preferably, a FIG. 3 (i.e., a front-elevation) display is selected, with a manipulable cursor to select and identify the estimated coordinate location of each point of pachymeter application to the cornea, an entry of thickness measurement being made into computer storage at module C for each different cursor-identified location. Typically, five points of thickness measurement are taken along each of several selected meridian courses through the central axis of the eye, and, in the event of corneal astigmatism (as is discernable from the FIG. 3 display of topography data generated by module A), it is recommended that the observed astigmatism-axis orientation be selected as the orientation for a central meridian of pachymeter measurements, with second and third successive sets of pachymeter measurements along meridians which are respectively offset 20 degrees on opposite angular sides of the central meridian of pachymeter measurement. Still further, it is recommended that the five pachymeter measurements on the central meridian be taken (a) at each of two outer limits which are about one millimeter short of intercept with the limbus, (b) at the center (i.e., on the optical axis of the eye), and (c) at the mid-points between the center and each of the respective outer limits; for the two meridians which are respectively at ±20 degrees offset from the central meridian, only four measurements are recommended (namely, the outer-limit and the mid-point measurements) because the central or optical-axis thickness measurement need only be made once and therefore would only be repeated if made for more than one meridian sweep.

Figure 2:
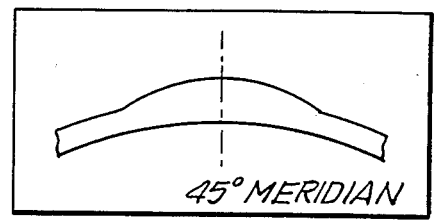
FIGS. 2, 3 and 4 are simplified diagrams to illustrate alternative displays at Module C of FIG. 1.

The third module C comprises a computer supplied by the topographical digital data (connection 10 from module A) and by the thickness digital data (connection 11 from module B). This computer, which may for example be an IBM PC computer, will be understood to have the necessary computer power to display the evaluated cornea in CAD/CAM fashion within the block of module C, as alternatively and diagrammatically shown in FIGS. 2, 3 and 4. The diagrammatic showing of FIG. 2 is for a full meridian section of the cornea (at least from limbus to limbus), and it will be understood that the computer has the capacity to so enlarge the scale of the sectional-display as to enable "close-up" examination of the detail of a selected fragment of the full section, namely as to precise local topography and thickness of the cornea.

Figure 4:
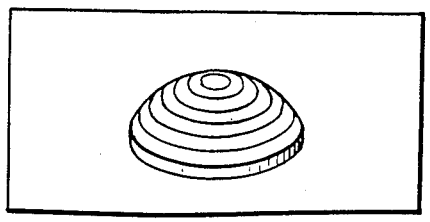

It will be understood that the digital data supplied in connections 10–11 to module C lends itself to alternative techniques of CAD/CAM display, as suggested in FIGS. 3 and 4; in FIG. 3, the cornea is displayed as if viewed from the anterior-posterior aspect (i.e., from front elevation), with alternating rings of progressively increasing thickness, in quantized increments, and in FIG. 4, the cornea is displayed as if viewed in perspective, with the isothickness contours of FIG. 3 shown in their correct perspective. The perspective of FIG. 4, coupled with the ability to selectively rotate the same via suitable software in the computer, will be seen to enable the surgeon to have a direct anterior-posterior viewing of the cornea as created for evaluation on the CRT screen of the computer. It will be further understood that with suitable software, the various displays of FIGS. 2, 3 and 4 may include numerical data which establish the aspect or angle of viewing display, as well as a numerical statement of local cornea thickness and/or curvature (anterior and/or posterior surface) and/or dioptric power, for any single point or series of points on the corneal surface. Such numerical data, as well as any of the various displays, will also be understood to be available for hard-copy print-out of any stage in the evaluation of the cornea.

Module D in FIG. 1 provides an additional CAD/CAM display (e.g., as in FIG. 5 or FIG. 6) which utilizes both the topographical and thickness measurement data supplied to Module C, as well as additional digitized information from another source, such as digitized data pertaining to idealized topography from a Module E, and/or digitized data from an operative-evaluation data bank, Module F.

Computer storage at Module E, which may be on a diskette usable as a source of data for part of the display at Module D, contains stored digitized data for the corneal topography of an idealized eye capable of creating emmetropia for the eye under evaluation for refractive surgical keratoplasty, considering the axial length of the eye determined by A-scan ultrasonography, the age and sex of the patient, intraocular pressure, and other factors which would allow close comparison of the evaluated eye with the projected idealized model emmetropic eye having similar or identical measurable parameters except for the proposed alteration in corneal curvature to obtain emmetropia. And by entering into Module E measured parameter data such as the age and sex of the patient, the axial (anterior-posterior) length of the eye (tenths of millimeters), the intraocular pressure of the eye, the resultant refractive condition desired (e.g., $-1.50$ diopters, $-1.00$ diopters, emmetropia, etc.), the desired surgical approach (incisional, such as radial keratotomy, or sculpting, etc.) and a selected data base for the eye (entered via suitable means suggested by Module E for the eye of the present concern, it becomes possible to create at Module D, and from the stored digitized data for the idealized eye, an additional display of the corneal profile of the idealized eye along the meridian selected for profile display of measured data at Module D. This feature permits the meridian profile for the idealized eye to be comparatively evaluated with respect to the display of the meridian profile for the measured-eye data (from connections 10-11).

Figure 5:
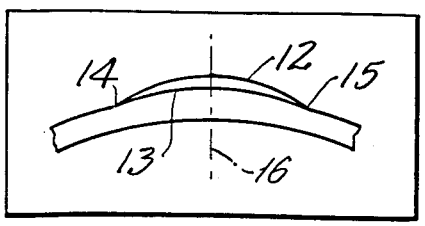
FIGS. 5 and 6 are simplified diagrams to illustrate alternatives for a CAD/CAM display at Module D in FIG. 1.

More specifically, FIG. 5 illustrates a Module D display wherein the measured eye is myopic, i.e., wherein the cornea profile 12 for the displayed meridian section of the measured eye is more curved and less flattened than the cornea profile 13 for the displayed meridian section of the idealized eye. In this circumstance, it is preferred to so orient the placement of profile 13 on profile 12 as to cause their near-limbus intersection. Thus, in FIG. 5, the points 14-15 of intersection of profiles 12-13 are at symmetrical offset on opposite sides of the optical axis 16, and the crescent-section area between profiles 12-13 represents that which must be excised if keratoplasty is to be by laser or other sculpting reduction of the cornea from profile 12 to profile 13. And if keratoplasty is to be by laser or by knife-cut radial keratotomy, the profile 13 is indicative of the target curvature to which it is necessary to effect cornea-curvature modification, to achieve or approach post-operative emmetropia.

Figure 6:
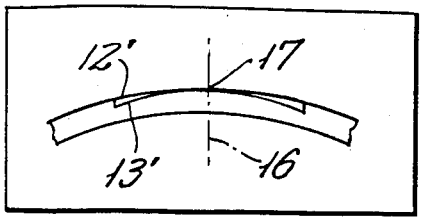

On the other hand, FIG. 6 illustrates a Module D display wherein the measured eye is hyperopic, i.e., wherein the cornea profile 12' for the displayed meridian section of the measure eye is more flat and less curved than the cornea profile 13' for the displayed meridian section of the idealized eye. In this circumstance it is preferred to so orient the placement of profile 13' on profile 12' as to cause their intersection only at intersection 17 with the optical axis 16, and the annular shape represented by the section area between profiles 12'-13' designates that which must be excised if the cornea is to be sculpted from the section profile 12' to the section profile 13'.

FIG. 1 further indicates that in lieu of the idealized topography data provided by Module E, or in suitably averaged conjunction therewith, an additional Module F may be drawn upon as a data bank, representing the surgeon's own experience record, from his prior experience records, and/or the totality of such records from a central data bank, serving the hospitals and ophthalmological facilities of a given geographic area, or for the country as a whole. Thus, (1) having performed an operation such as a radial keratotomy, with 8 radial incisions of 3-mm length, from an inner radial limit of 2-mm, to an outer radial limit of 5-mm, and with what he believes with his manual skill was to a reasonably uniform depth of 0.52-mm, (2) having used the analysis equipment of FIG. 1 to reexamine the eye after corneal surgery, and (3) finding that he caused the measured-eye profile 12 at selected meridian sections to substantially conform to the idealized eye profile 13, he can enter into storage at Module F the pertinent parameters of the eye before and after surgery, as well as the pertinent parameters of his operative procedure. And upon later inspection of the same eye, he can similarly enter into storage at Module F any further observations as to longer-term effects attributable to the operation. Such recorded data, along with the surgeon's use of other techniques to secure the same or a substantiallly equivalent result for another patient, can also be entered into storage at Module F, so that in the course of time the data bank will accumulate a fund of experience from which alternative techniques and their after-effects can be part of the available background for optimized pre-surgery decision-making. It will of course be understood that the call up of data from Module E and/or from Module F for display at Module D may involve graphical two-dimensional display of selected meridian sections, as well as written display (a) of pertinent parameters of the relevant eye (before and after surgery), (b) of pertinent parameters and notes of the involved operative procedure, and (c) of observed long-term after-effects.

In the event that the surgeon decides to use automated scanning-laser apparatus, as of the character described in my said copending application Ser. No. 552,983, to perform corneal surgery, whether the correction is to reduce or eliminate a myopia or a hyperopia, the stored decisional data for the pertinent parameters of the operation will be available for total adoption (or for adoption with deliberate modification) via Module D. Thus, an output connection 18 from Module D to Module G will be understood to show use of such parameters as control parameters for automated operation of laser-incisional/sculpting displacements via Module G. The stored and available parameter data supplied via connection 18 will be understood to include such laser-operating data as power level, exposure rate (i.e., laser-pulse repetition rate), spot size and the like; and of course having performed the operation, the operating-parameter data as well as the before/after eye data will be enterable in the data bank at Module F, should the surgeon decide that the success (or other outcome) of the operation merits such retention of data.

It will be seen that the described apparatus and methods meet all stated objects and portend a major change in approach to correction of corneal-refractive problems. The objective of the eye measurements is realized by creating a digitized data base which describes corneal profiles, illustratively available for display for any of a plurality of meridian sections. These data are available in both graphical and written display and may be up-graded by experience, to enable a well-informed base for decision-making prior to surgery; the digitized decisional data are directly utilizable for the modeling of incisions (whether radial or full sculpture), or to provide automated directions for incision or ablative sculpting. The data may be displayed on hard-copy print-out or on a CRT screen as a guide for the surgeon's incisions, or to direct an incisional or sculpting laser system.

It will be understood that the automated use of Module G lends itself to perform a single operative procedure to effect the entire refractive correction indicated by a display as in FIG. 5 or FIG. 6. Alternatively, and certainly until the surgeon has developed full confidence in use of the automated surgery available to him, he may opt to modify the surgery in the conservative direction of excising merely a fraction, e.g., one half, of the corneal tissue indicated for removal. In this latter event, he can make another measurement evaluation of the eye before deciding to proceed with the completing half of the total operation. In other words, by following the automated pattern of tissue removal, but only to one half the programmed varying depth of ablation, he can see what refractive correction was achieved and thus be in a position to judge whether the remaining half of the total procedure (i.e., second operation) should be (a) to the same, (b) to a greater or (c) to a lesser fraction of the programmed varying depth.

An important feature of the invention is the data-bank function that provides a supplement to measured data from the corneal-evaluation/analysis Modules A, B and C. Module D enables the comparative display of the evaluation/analysis data, in context with the data-bank output available from Module F. Significantly, these data enable the computer at Module D to suggest the appropriate length and depth of radial keratotomy incisions, the placement of "T" incisions or relaxing limbal incisions, or any combination of all of the incisional refractive surgical procedures now available anywhere in the world. In this manner, the computer can suggest to the surgeon the course of surgical action that would reduce the refractive error—whether it be myopic, hyperopic, or astigmatic—in order that the eye may be rendered emmetropic or slightly myopic or even slightly hyperopic. In this manner, the surgeon has the option to accept the recommendation of the computer for his surgical intervention on that particular cornea, as obtained from a nation-wide or broad data base. As the surgeon increases his prowess and the number of cases performed, his particular manipulative surgical technique becomes entered in the computer as a function entirely separate and unique for him. As his individual data base increases, the computer can recognize his tendency for a slightly deeper incision, wider incision, or other peculiarities of this individual technique. Therefore, by inserting a plastic "credit-like" card, the computer can be made to recognize the individual surgeon and call forth his particular data base, or a more general hospital, city-wide, or larger data-base population. All corrective suggestions by the computer to produce a particular dioptric end result following surgery can be displayed in a CAD/CAM fashion and are capable of hard-copy print-out. Various suggestions by the computer, adopted and corroborated by the surgeon, can also be printed immediately for use in the surgical suite.

Although the indicated presently available pachymeters contemplate corneal thickness measurement at a plurality of locations on the corneal surface, including plural locations (e.g., five) along a given meridian section, even this relatively small number of points on a curve will be understood to establish a useful presentation of the curve, particularly in reference to the much more accurately developed topography data for the anterior surface of the cornea. Thus, the accurate exterior-surface data, taken with the relatively few points of pachymeter data, will enable reasonably accurate digitized availablity of the concave typography of the cornea, should the surgeon see fit to model the same in his CAD/CAM display, whether the modeling be by meridian section (FIG. 2), elevational aspect (FIG. 3), or rotatable 3-D model (FIG. 4). In the latter event, the modeling at FIG. 4 may include "wire-connected" modeling of both the concave and the convex topographies, in either true-scale thickness offset from each other, or in a displayed offset relation wherein the measured thickness is exaggerated (but scaled), e.g., at twice or ten times the measured values.

What is claimed is:

1. The method of using a digital computer to correctively improve optical properties of an eye by changing the curvature of the anterior surface of the cornea in approach to a computer-stored digital definition of an idealized three-dimensional anterior-surface curvature, which method comprises:
   (a) determining and digitizing the topography of the anterior surface of the cornea as a three-dimensional curved surface, and entering digitized topography data thereof into computer storage;
   (b) creating from said topography data and from said stored digital definition a displayed numerical statement of the spherical and cylindrical-components of difference bewteen the determined and the idealized curvatures, whereby the displayed numerical statement is also a statement which is definitive of a characterized volumetric removal of corneal tissue necessary to proceed from the determined to the idealized curvature;
   (c) directing ultraviolet laser radiation to the anterior surface of the cornea to selectively ablate the same by photodecomposition; and
   (d) using said computer-storage data to control the laser radiation to achieve a curvature change in approach to the diealized surface curvature in a volumetric removal of tissue from the anterior surface and with penetration into the stroma.

2. The method of claim 1, in which said numerical statement is in diopters.

3. The method of claim 1, in which a modification of said numerical statement is entered into computer storage and is used as the basis of control of step (d), said modificaton being in the form of a digital definition of a three-dimensional anterior-surface curvature which is intermediate the determined and the idealized curvatures.

4. The method of claim 1, wherein the computer-stored digital definition of an idealized curvature is the product of a memory bank reflecting entries specific to prior corneal-sculpture operations which have been deemed successful.

5. The method of using a digital computer to correctively improve optical properties of an eye by changing the curvature of the anterior surface of the cornea, which method comprises:
(a) determining and digitizing the topography of the anterior surface of the cornea as a three-dimensional curved surface, and entering digitized topography data thereof into computer storage;
(b) entering into computer storage, as another three-dimensional curved surface, digitized data for the anterior-surface topography of an idealized cornea wherein optical improvement is the achievement objective based on measured parameter data for the eye, whereby computer storage contains digitized data which is definitive of a characterized volumetric removal necessary to proceed from one to the other of said curved surfaces;
(c) directing ultraviolet laser radiation to the anterior surface of the cornea to selectively ablate the same by photodecomposition; and
(d) using said computer-storage data to control the laser radiation to achieve said other curved surface in a volumetric removal of tissue from the anterior surface and with penetration into the stroma.

6. The method of claim 5, in which emmetropia is the achievement objective of step (b).

7. The method of claim 5, in which the achievement objective of step (b) is a three-dimensional curved surface which represents a predetermined fractional change toward achieving an ultimate optical property of substantial emmetropia for the involved eye, whereby an opportunity is presented to evaluate optical and/or topographical features of the eye after completion of step (d) to determine the degree to which the achieved fractional change conforms to the predetermination thereof.

8. The method of claim 5, in which separate visual displays are created for corresponding viewing aspects of the stored digitized data of step (a) and for the stored digitized data of step (b).

9. The method of claim 5, wherein the following additional steps are performed:
(e) an optical determination is made as to whether step (d) has produced substantial emmetropia, and if substantial emmetropia has been achieved, a digital determination is made of the topography of the thus-improved anterior surface of the cornea, with said digital determination and associated laser-control data being entered into computer storage, the digitized storage entry for this step (e) being one of a plurality of entries wherein each entry is applicable to a different eye for which the procedure of steps (a) through (d) has produced substantial emmetropia;
(f) averaging the stored plural-eye data to thereby provide topography data for an idealized eye; and
(g) using the idealized eye data of step (f) in step (b) of a subsequent performance of the method of claim 5 in application to another eye.

10. The method of using a digital computer to correctively improve optical properties of an eye by changing the curvature of the anterior surface of the cornea, which method comprises:
(a) measuring and digitizing the topography of the anterior surface of the cornea as a three-dimensional curved surface, and entering digitized topography data thereof into computer storage;
(b) creating from the stored digitized topography data a center-identified display of the front elevation of the cornea;
(c) creating on said display a straight marker line along a meridian through the center of the display and at a slected orientation;
(d) entering into computer storage digitized data for the corneal topography of an idealized eye wherein emmetropia is the achievement objective;
(e) creating from the stored digitized data for the measured eye and for the idealized eye a coordinated display of both curvature along said meridian, whereby computer storage contains digitized data which is definitive and said coordinated display is visually indicative of a characterized volumetric removal of corneal tissue necessary to proceed from the measured curvature toward the idealized curvature;
(f) directing ultraviolet laser radiation to the anterior surface of the cornea to selectively ablate the same by photodecomposition; and
(g) using said computer-storage data to control the laser radiation to approach the idealized curvature in a volumetric removal of tissue from the anterior surface and with penetration into the stroma.

11. The method of claim 10, wherein the meridian marker line of step (c) is selectively rotatable about the center of the display, whereby astigmatism can be visually apparent in the coordinated display of step (e).

12. The method of claim 10, wherein for the case of a given eye that is hyperopic and therefore requires an idealized-eye meridional profile which is more curved and less flat than the meridional profile of the idealized eye, the coordination of the display of step (d) is caused to position the eye-axis intercept of the idealized-eye meridian profile to coincide with the eye-axis intercept of the meridian profile of the measured eye.

13. The method of claim 10, wherein for the case of a given eye that is myopic and therefore requires an idealized-eye meridional profile which is more flat and less curved than the meridional profile of the idealized eye, the coordination of the display of step (d) is caused to position the idealized-eye meridian profile to intersect with the meridian profile of the measured eye at points symmetrically spaced on opposite sides of the optical axis of the eye and near but short of the limbus region of the cornea.

* * * * *

UNITED STATES PATENT AND TRADEMARK OFFICE
CERTIFICATE OF CORRECTION

PATENT NO. : 4,669,466
DATED : June 2, 1987
INVENTOR(S) : Francis A. L'Esperance It is certified that error appears in the above-identified patent and that said Letters Patent are hereby corrected as shown below:

Column 2, line 18, correct "ablotion" to --ablation--.

Column 8, line 58, correct "bewteen" to --between--.

Column 9, line 1, correct "diealized" to --idealized--.

Column 9, line 9, correct "modificaton" to --modification--.

Column 10, line 30, correct "curvature" to --curvatures--.

Signed and Sealed this

Twenty-second Day of September, 1987

Attest:

DONALD J. QUIGG

Attesting Officer   Commissioner of Patents and Trademarks